United States Patent [19]

Bamberger et al.

[11] Patent Number: 4,584,994
[45] Date of Patent: Apr. 29, 1986

[54] ELECTROMAGNETIC IMPLANT

[76] Inventors: Charles Bamberger, 1400 S. Main St., #105; James W. Tunstill, 1400 S. Main St., #512, both of Fort Worth, Tex. 76104

[21] Appl. No.: 537,785

[22] Filed: Sep. 30, 1983

[51] Int. Cl.⁴ .............................................. A61F 5/00
[52] U.S. Cl. ..................................... 128/79; 128/1 R; 310/40 MM; 623/24; 623/26
[58] Field of Search ...................... 128/1.3–1.5, 128/79, DIG. 25, 1 R; 604/891; 310/86, 40 MM; 3/1.7, 1

[56] References Cited

U.S. PATENT DOCUMENTS

| | | | |
|---|---|---|---|
| 2,766,695 | 10/1956 | Gailloud | 310/86 |
| 3,513,486 | 5/1970 | DeBennetot et al. | 3/1.7 |
| 3,608,088 | 9/1971 | Dorman et al. | 3/1.7 |
| 3,750,194 | 8/1973 | Summers | 128/DIG. 25 |
| 3,817,237 | 6/1974 | Bolduc | 128/1 R |
| 3,954,102 | 5/1976 | Buuck | 128/79 |
| 4,342,308 | 8/1982 | Trick | 128/79 |
| 4,424,807 | 1/1984 | Evans, Sr. | 128/79 |

OTHER PUBLICATIONS

Roller Pump Theory–1/1/72–p. 1.7.

*Primary Examiner*—C. Fred Rosenbaum
*Assistant Examiner*—Mario Costantino
*Attorney, Agent, or Firm*—James E. Bradley

[57] ABSTRACT

An apparatus for performing a specified task within the human body has an implanted electromagnetic device for use in conjunction with an external electromagnetic field. The electromagnetic device includes a drive member which is a rotor of an electric motor. The drive member, when located within an electromagnetic field, will drive a pump to pump fluid from a reservoir such as to a pair of prosthesis cylinders implanted in the penis. The external electromagnetic field is an AC stator that has an aperture for positioning over the rotor, which is located in a sealed housing implanted in the scrotum.

2 Claims, 4 Drawing Figures

ELECTROMAGNETIC IMPLANT

BACKGROUND OF THE INVENTION

1. Field of the Invention

This invention relates in general to an implant in the human body for performing a specified task, and in particular to an electromagnetically driven pump for use with a penile prosthesis.

2. Description of the Prior Art

There are a number of tasks which an implant in the human body could perform when stimulated externally. One such use is with an inflatable penile prosthesis, which enables impotent males to achieve erection. This prosthesis has two elastomeric, inflatable cylinders that are inserted within the corpora cavernosa of the penis. These cylinders are connected by tubing to a manual pump implanted in the scrotum. Tubing extends from the pump to a reservoir implanted in the abdominal cavity. The reservoir contains a liquid which can be pumped to the cylinders by squeezing the pump. A valve located in conjunction with the pump allows fluid to return to the reservoir when it is squeezed. While this type of device is successful, it is sometimes difficult to manipulate, particularly for older or arthritic persons.

SUMMARY OF THE INVENTION

An electromagnetic drive means is implanted within the human body for performing specified tasks, such as pumping fluid to a penile prosthesis. The implanted assembly includes a drive member mounted within a sealed housing implanted within the body. In the preferred embodiment, the drive member is an AC (alternating current) rotor of the type that will rotate when placed within an AC electromagnetic field. The assembly is preferably implanted in a portion of the body containing thin loose skin, such as the scrotum. The portion of the housing containing the rotor can be manipulated to draw the skin tightly over the rotor, defining a protuberance.

An external electromagnetic field is used in conjunction with the implanted assembly. The electromagnetic field is an AC stator having an aperture that is sized to fit over the protuberance of the implanted rotor. The electromagnetic field is connected to conventional AC power, and when placed over the protuberance will cause the rotor to rotate. A rotary pump is connected to the rotor through a drive means. The pump will pump liquid to the cylinders, or to the reservoir, depending upon the positioning of the external stator field.

DESCRIPTION OF THE PREFERRED EMBODIMENT

Figure 1:
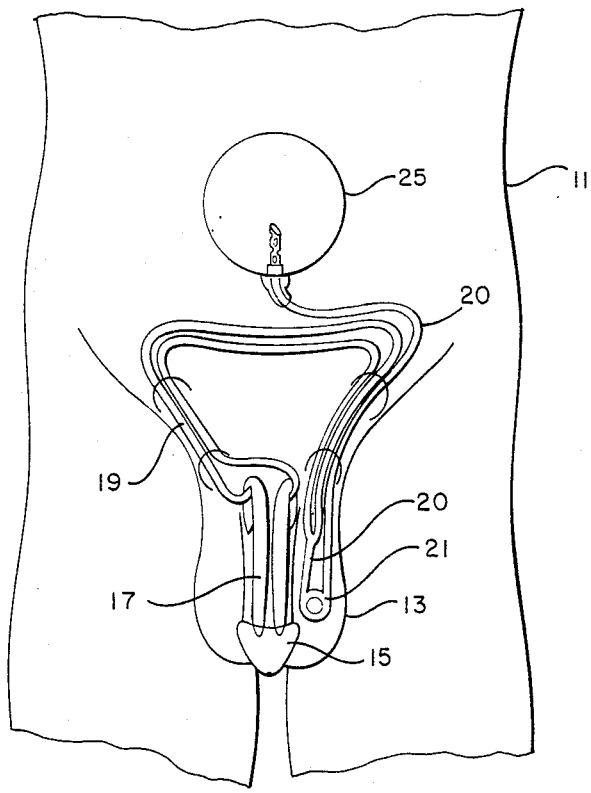
FIG. 1 is a schematic view of a portion of the male human body showing a penile prosthesis implanted in accordance with this invention.

Referring to FIG. 1, the numeral 11 refers to the human male, with the numeral 13 designating the scrotum and numeral 15, the penis. The penile prosthesis includes a pair of inflatable, elastomeric cylinders 17. Each cylinder is located in a corpora cavernosum of the penis as described in U.S. Pat. No. 3,954,102, Buuck, issued May 4, 1976. A flexible tube 19 extends from each cylinder 17 to a tube 20. Tube 20 extends through a pump assembly 21 that is implanted in the scrotum 13. From pump assembly 21, tube 20 extends through a reservoir 25 located in the abdominal cavity. Reservoir 25 contains a liquid which when pumped into the cylinders 17 causes an erection of the penis 15. Pumping the liquid in the opposite direction, returning fluid to the reservoir 25, causes the penis 15 to return to its normal flaccid state.

Figure 2:
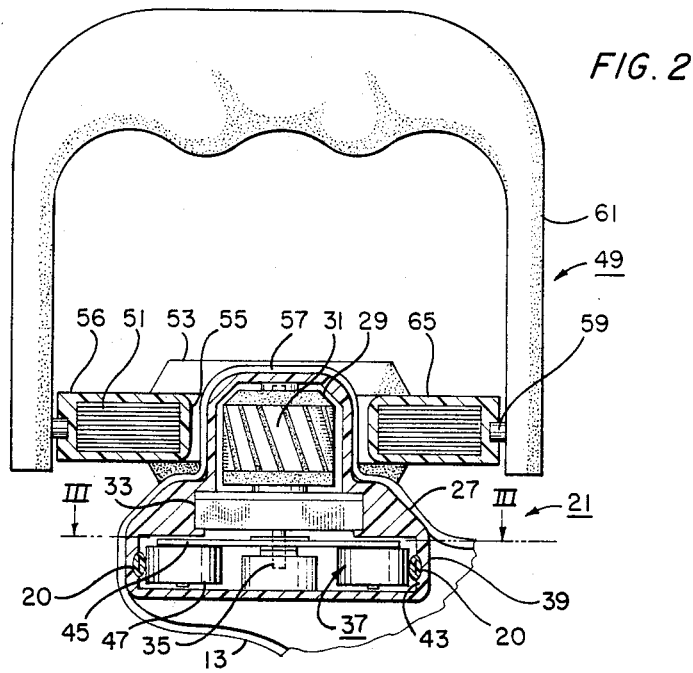
FIG. 2 is an enlarged, partially sectioned view of the implanted assembly and the external electromagnetic stator position over the assembly.

Referring to FIG. 2, the pump assembly 21 is located within a sealed housing 27 implanted in scrotum 13. An electric motor rotor 29 is rotatably mounted within housing 27. Rotor 29 is preferably the rotor portion of an AC alternating current-shaded pole motor, so designed that the AC electromagnetic field of an externally applied stator will cause it to rotate. Rotor 29 is comprised of ferrous metal laminations or disks stacked. A plurality of inclined copper strips 31 extend about its cylindrical exterior and are located in grooves formed in the sidewall of the rotor 29. Strips 31 are parallel with each other and incline at about a 20° angle with respect to the axis of rotor 29.

Rotor 29 is connected to a gear reduction chain or box 33. The gear reduction box 33 is not shown in detail, but comprises a number of different diameter gears interconnected together in a conventional manner to an output shaft 35. The gears will be sized so as to provide an increased torque, but lower speed output on shaft 35 than rotor 29.

Figure 3:
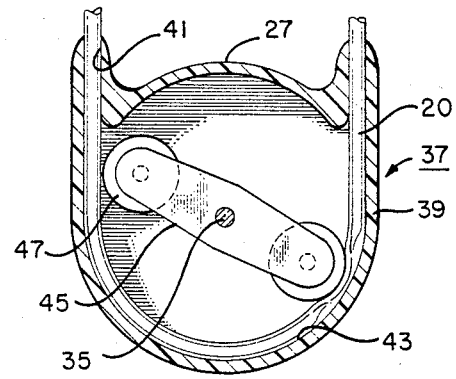
FIG. 3 is a sectional view of the implanted assembly taken along the line III—III of FIG. 2.

Output shaft 35 drives a rotary pump 37 for supplying fluid selectively to the cylinders 17 or to the reservoir 25. As shown in FIG. 3, pump 37 is located within a semi-cylindrical portion 39 of the housing 27, which has a larger diameter than the portion containing rotor 29. Housing portion 39 has two passages 41. One passage sealingly receives the tubing 20 which extends to cylinders 17 (FIG. 1), while the other passage sealingly receives the portion of tubing 20 which extends to reservoir 25 (FIG. 1). Housing portion 39 has an interior semi-cylindrical interior wall 43. The tubing 20 extends in a loop in the housing portion 39, and lies against the wall 43. The output shaft 35 is concentric within the wall 43.

A linkage member 45 is secured perpendicular to output shaft 35 for rotation therewith. Linkage member 45 carries on opposite ends rollers 47. Each roller 47 will rotate with respect to linkage member 45. The axis of each roller 47 is 180 degrees apart from the opposite roller 47. Linkage member 45 is of a length such that the rollers 47 will be in close proximity to the interior wall 43 when rotated. Each roller 47 will squeeze the tubing 20 against the wall 43 to push or pump liquid in the direction of rotation. Each roller 47 pumps the fluid for one-half of a revolution. Each roller 47 engages the tube 20 slightly before the opposite roller completes its stroke. Regardless of the position of output shaft 35, one roller 47 will always be in tight contact with the tube 20, squeezing it against wall 43 and preventing any flow through the point of constriction. Consequently, rollers 47 also serve as a valve to prevent flow in either direction when the output shaft 35 is stopped.

Referring again to FIG. 2, the external stimulation for the rotor 29 is an AC stator electromagnetic field winding 49. Stator 49 is the stationary stator portion of an AC-shaded pole motor of a type commonly used in electric fans. Stator 49 includes a plurality of ferrous metal plates or disks 51 stacked in electrical contact with each other. A hole (not shown) is formed on one side of the stack of disks 51 and a coil 53 of copper wire is wound through this hole and around one edge of the stack of disks 51. The copper wire coil 53 has many turns of wire wrapped through and around the disks 51. Connecting thee coil to AC voltage causes the disks 51 to become electromagnetic, creating an AC electromagnetic field.

An aperture 55 is provided in the disks 51 for receiving the rotor 29. The disks 51 and coil 53 are covered by a plastic cover 56. Aperture 55 is the bore of stator 49 and when coil 53 is energized, the electromagnetic field within aperture 55 will cause the rotor 29 to rotate if it is located therein. The polarity created in aperture 55 by coil 53 is such that if side 65 of stator 49 faces away from pump 37, the rotor 29 will rotate in one direction. If side 65 faces toward pump 37, the polarity is reversed and rotor 29 rotates in the opposite direction. The aperture 55 is large enough so that it will receive not only the cylindrical portion of the housing 27 that contains rotor 29, but also the skin 57 of the scrotum 13. The electromagnetic field will pass through cover 56, skin 57 and housing 27.

Figure 4:
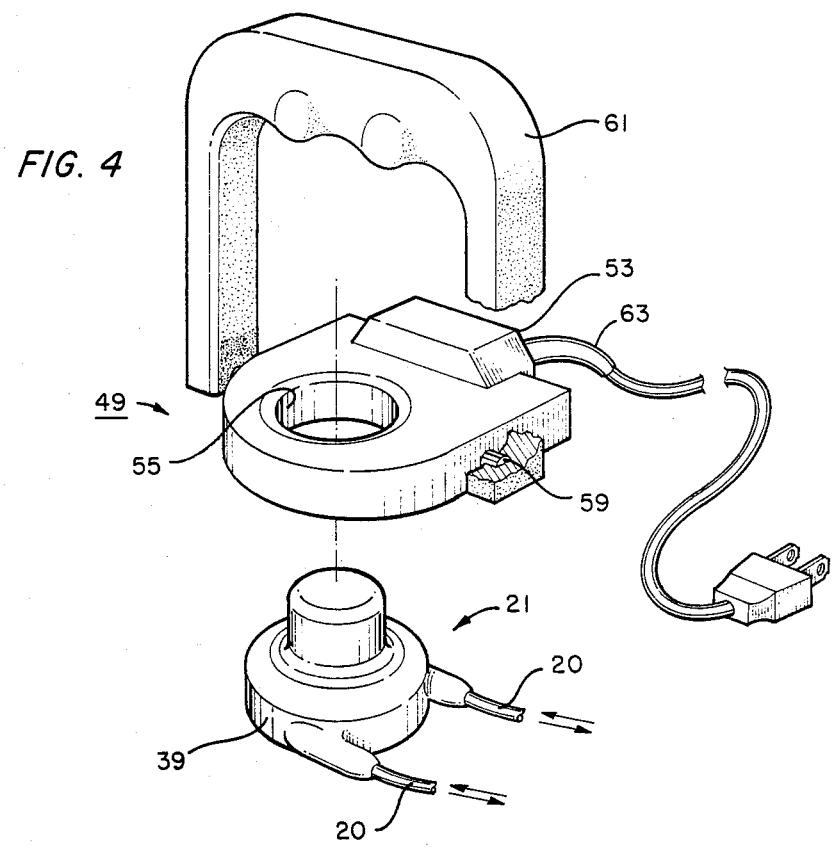
FIG. 4 is a perspective view of the stator and the internal pump assembly removed from the body.

The stator 49 is secured by pivot pins 59 to a handle 61. The pivot pins enable the handle 61 to rotate at least 180 degrees with respect to the stator 49. An electrical cord 63, shown in FIG. 4, has a conventional plug for connecting 120 volt AC power to coil 53.

In operation, to cause an erection, the implanted housing 27 is positioned so that the skin 57 of scrotum 13 is drawn tightly over the portion of the housing containing rotor 29, creating a generally cylindrical protuberance. Then, the user places the stator 49 over and radially around the protuberance so that its axis will coincide with the axis of rotor 29. The cylindrical side wall of rotor 29 will be fully contained within the cylindrical side wall of aperture 55. The side 65 (FIG. 2) of the stator 49 is shown facing away from the body. The user then plugs the cord 63 into the AC power. An electromagnetic field is created in aperture 55, which induces an electromagnetic field through the skin 57 and housing 27 to cause the rotor 29 to rotate. The field radially drives the rotor 29. Rotor 29 drives the gear box 33, which rotates the output shaft 35 to pump fluid to the cylinders 17 (FIG. 1). Fluid will pass from the reservoir 25 to the cylinders 17 until fluid from reservoir 25 is contained within the cylinders 17, obtaining an erection of the penis 15. The stator 49 is then removed. The rollers 47 will maintain fluid pressure in the cylinders 17 due to the constriction that one of them will create in the tube 20.

To reverse the procedure, the handle 61 is rotated 180 degrees with respect to the stator electromagnet 49, reversing the orientation of side 65 of stator 49 with respect to rotor 29. Skin 57 of scrotum 13 is drawn over the housing 27 and the stator 49 is placed around the protuberance. In the reverse procedure, the side 65 will be facing toward the body 11 (FIG. 1), instead of away. This creates an electromagnetic field when plugged into AC power which causes the rotor 29 to rotate in the opposite direction than previously described. The rotary pump 37 pumps the fluid in the opposite direction back into the reservoir 25, collapsing cylinders 17.

The invention has significant advantages. The pump is easily operated, requiring little skill in manipulation. Persons with stiff arthritic fingers would have less difficulty operating the assembly than the prior art manual type. The implanted electromagnetic motor has other possible applications such as in the quantitative delivery of medications (with modifications for metering). Insulin, heparin, anesthetics or chemotherapeutic agents could be stored in a reservoir and delivered to a selected region. The motor assembly could also be used to activate and deactive any artificial body sphincters.

While the invention has been shown in only one of its forms, it should be apparent to those skilled in the art that it is not so limited but is susceptible to various changes without departing from the scope of the invention.

We claim:

1. In a penile prosthesis of the type having at least one inflatable cylinder adapted to be implanted in a penis and a reservoir containing fluid implanted in the user's body for supplying fluid through a flexible tube to the cylinder to erect the penis, an improved apparatus for pumping the fluid between the reservoir and cylinder, comprising:

a sealed housing adapted to be implanted in a scrotum;

an alternating current electric motor rotor having a cylindrical sidewall and mounted within the sealed housing, the sealed housing being positioned such that skin of the scrotum may be pulled tightly over a portion of the housing containing the rotor to define a protuberance protruding from the body;

a semi-cylindrical interior wall formed in the housing, the housing having passages which receive a loop of the tube, which lies alongside the interior wall;

gear reduction means connected to the rotor and having an output shaft located concentrically within the interior wall, for transmitting higher speed rotation of the rotor to lower speed higher torque output on the shaft;

linkage means connected to the shaft for rotating with the shaft a pair of rollers opposite each other and in close proximity to the interior wall, to squeeze the tube against the wall and pump fluid to and from the reservoir depending upon the direction of rotation; and an alternating current electromagnetic field generating means for creating an electromagnetic field, the electromagnetic field means adapted to be located exterior of the body and having aperture means for positioning the electromagnetic field generating means radially around the protuberance to cause the rotor to rotate;

the aperture means of the electromagnetic field generating means comprising a cylindrical bore formed within a plurality of stator disks and which is adapted to receive the protuberance and surrounds the sidewall of the rotor entirely;

the electromagnetic field generating means polarizing the bore in the stator disks such that when the disks are placed over the protuberance with a first side facing toward the user's body the rotor will rotate in one direction, and when the disks are placed over the protuberance with the first side facing away from the user's body, the rotor will rotate in the opposite direction.

2. An improved method for pumping fluid from a reservoir adapted to be implanted in a human body, comprising in combination:
- implanting a sealed housing in a scrotum;
- placing in the sealed housing a magnetic drive means and a pump means, and connecting the pump means to the reservoir;
- implanting in the human body a penile prosthesis of the type having at least one inflatable cylinder, and connecting the prosthesis to the reservoir and to the pump means;
- stretching the skin of the scrotum over the magnetic drive means, defining a protuberance extending outwardly from the scrotum; and
- providing an electromagnetic field generating means for rotating the magnetic drive means, and positioning the electromagnetic field generating means radially around the protuberance to cause the magnetic drive means to selectively rotate the pump means to pump fluid from the reservoir to the prosthesis to inflate the prosthesis and to pump fluid from the prosthesis to the reservoir to deflate the prosthesis.

* * * * *